US005653692A

United States Patent [19]
Masterson et al.

[11] Patent Number: 5,653,692
[45] Date of Patent: Aug. 5, 1997

[54] METHOD AND SYSTEM FOR DIRECT HEATING OF FLUID SOLUTION IN A HOLLOW BODY ORGAN

[75] Inventors: Steven P. Masterson, San Francisco; Robert J. Laird, Richmond, both of Calif.

[73] Assignee: Innerdyne Medical, Inc., Sunnyvale, Calif.

[21] Appl. No.: 525,436

[22] Filed: Sep. 7, 1995

[51] Int. Cl.⁶ .................................................. A61F 7/12
[52] U.S. Cl. .......................... 604/113; 604/114; 604/49; 606/27; 607/113; 607/138
[58] Field of Search ........................ 604/113, 114, 604/96, 118, 105, 107, 49; 606/33, 49, 27, 32; 607/113, 122, 138

[56] References Cited

U.S. PATENT DOCUMENTS

| | | |
|---|---|---|
| 4,375,220 | 3/1983 | Matvias . |
| 4,430,076 | 2/1984 | Harris . |
| 4,469,103 | 9/1984 | Barrett . |
| 4,676,258 | 6/1987 | Inokuchi et al. . |
| 4,955,377 | 9/1990 | Lennox et al. . |
| 4,979,948 | 12/1990 | Geddes et al. . |
| 5,045,056 | 9/1991 | Behl . |
| 5,100,388 | 3/1992 | Behl et al. . |
| 5,159,925 | 11/1992 | Neuwirth et al. . |
| 5,188,602 | 2/1993 | Nichols . |
| 5,191,883 | 3/1993 | Lennox et al. ............... 128/401 |
| 5,195,965 | 3/1993 | Shantha . |
| 5,222,938 | 6/1993 | Behl . |
| 5,242,390 | 9/1993 | Goldrath . |
| 5,257,977 | 11/1993 | Eshel . |
| 5,273,526 | 12/1993 | Dance et al. ............... 604/35 |
| 5,275,597 | 1/1994 | Higgins et al. ............... 606/33 |
| 5,277,201 | 1/1994 | Stern . |
| 5,284,486 | 2/1994 | Kotula et al. ............... 606/159 |
| 5,368,591 | 11/1994 | Lennox et al. . |
| 5,370,644 | 12/1994 | Langberg ............... 606/33 |
| 5,423,797 | 6/1995 | Adrian et al. ............... 606/1 |
| 5,501,694 | 3/1996 | Ressemann et al. ............... 606/159 |
| 5,507,795 | 4/1996 | Chiang et al. ............... 606/167 |

FOREIGN PATENT DOCUMENTS

| | | |
|---|---|---|
| 4123-418-A | 4/1992 | Germany . |
| 1319848-A1 | 6/1987 | U.S.S.R. . |
| WO 81/03616 | 12/1981 | WIPO . |

OTHER PUBLICATIONS

Becker, et al., "Long Term Occlusion of the Porcine Cystic Duct by Means of Endoluminal Radio Frequency Electrocoagulation," *Radiology*, 167:63–68, 1988.

Becker, et al., "Gall Bladder Ablation Through Radio Logic Intervention Choela and Experimental Alternative to Cholecystomy," *Radiology*, 171:235–240, 1989.

Fram, et al., "In Vivo Radio Frequency Thermal Balloon Angioplasty of Porcine Coronary Arteries; Histologic Effects and Safety," *American Heart Journal*, 126:969–978, 1993.

Heads Up, Product Brochure, "Heated Balloon Catheters," 1994.

Yamanashi, et al., "Properties of Electromagnetic Field Focusing Probe," *The Journal of Vascular Diseases*, pp. 953–954, Nov. 1988.

*Primary Examiner*—Corrine M. McDermott
*Assistant Examiner*—Cris L. Rodriguez
*Attorney, Agent, or Firm*—Townsend and Townsend and Crew LLP

[57] ABSTRACT

The invention provides improved methods and devices for heating a thermally conductive fluid within an internal body organ to thermally ablate or necrose the body organ. In an exemplary embodiment, the invention provides a thermal ablation device having an elongate member with a proximal end and a distal end. A heating apparatus is provided near the distal end of the elongate member which is constructed to heat a thermally conductive fluid without substantial direct heating of the heating apparatus. A fluid circulator is provided near the heating apparatus which circulates the thermally conductive fluid past the heating apparatus.

50 Claims, 7 Drawing Sheets

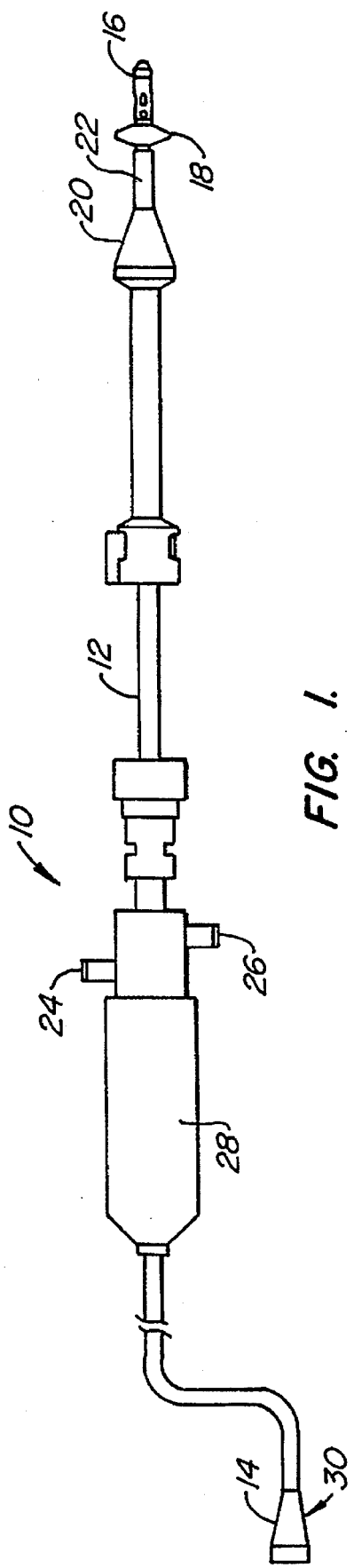
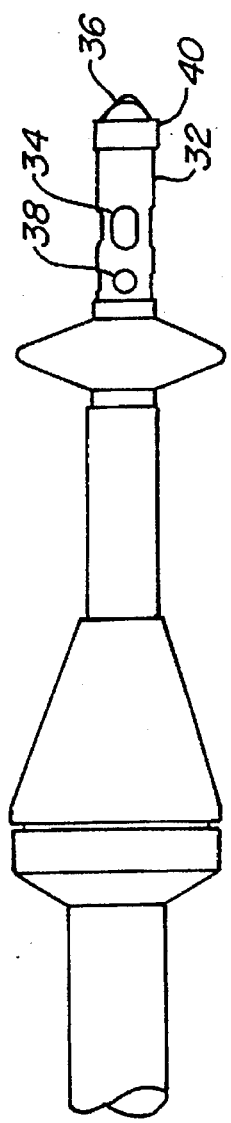
FIG. 1.
FIG. 2.

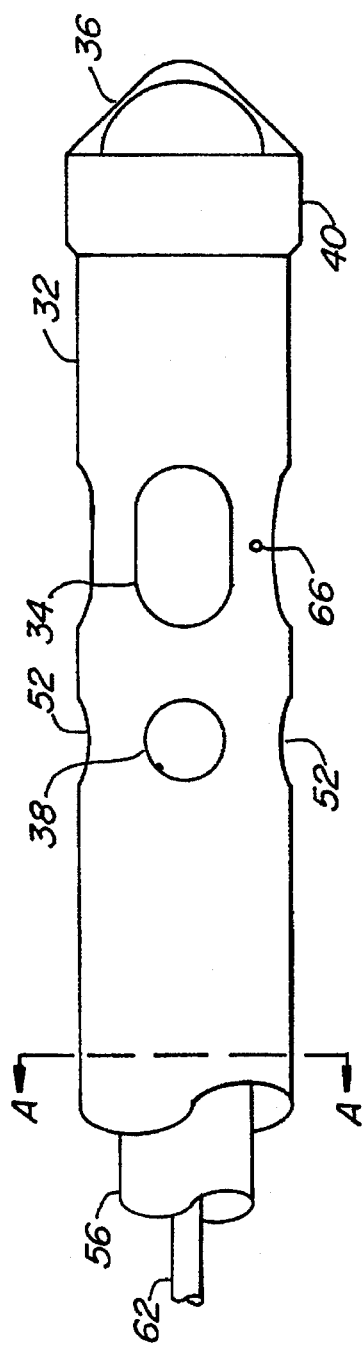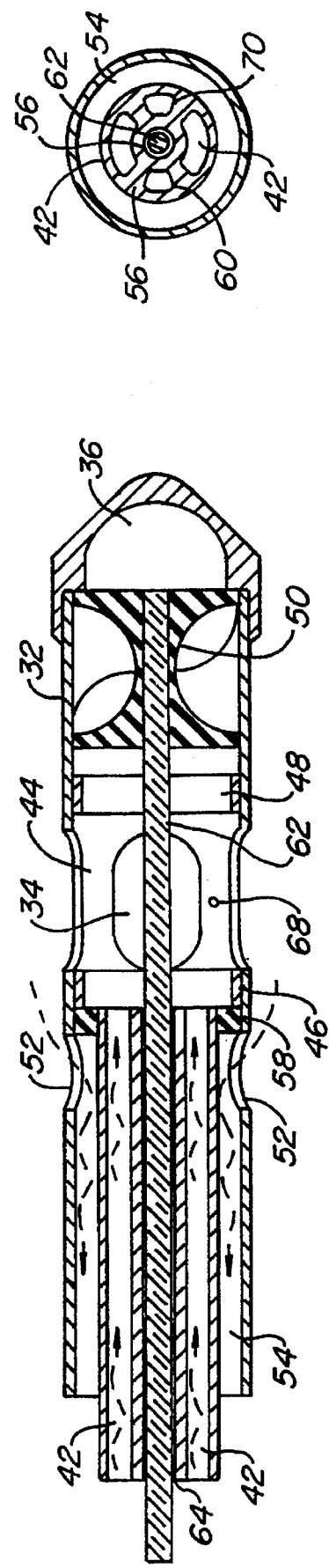
FIG. 3.
FIG. 3A.
FIG. 4.

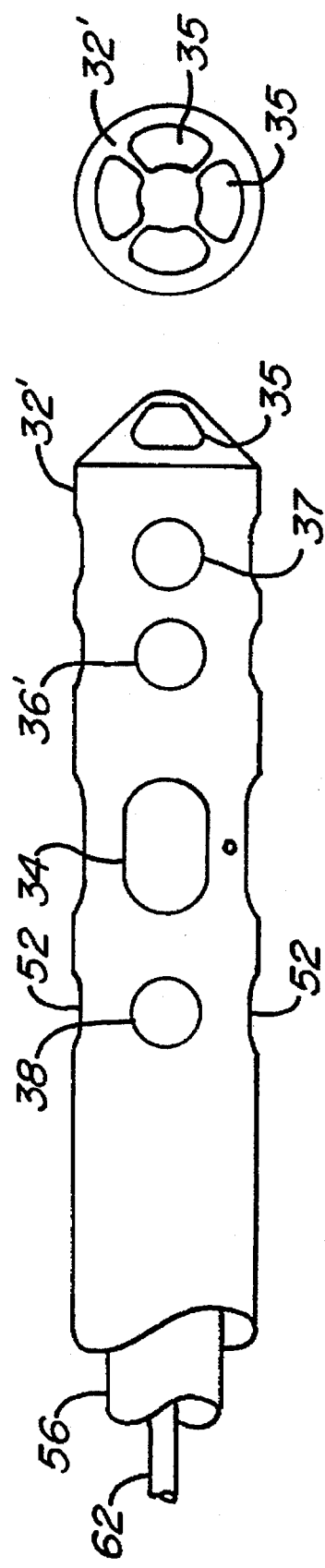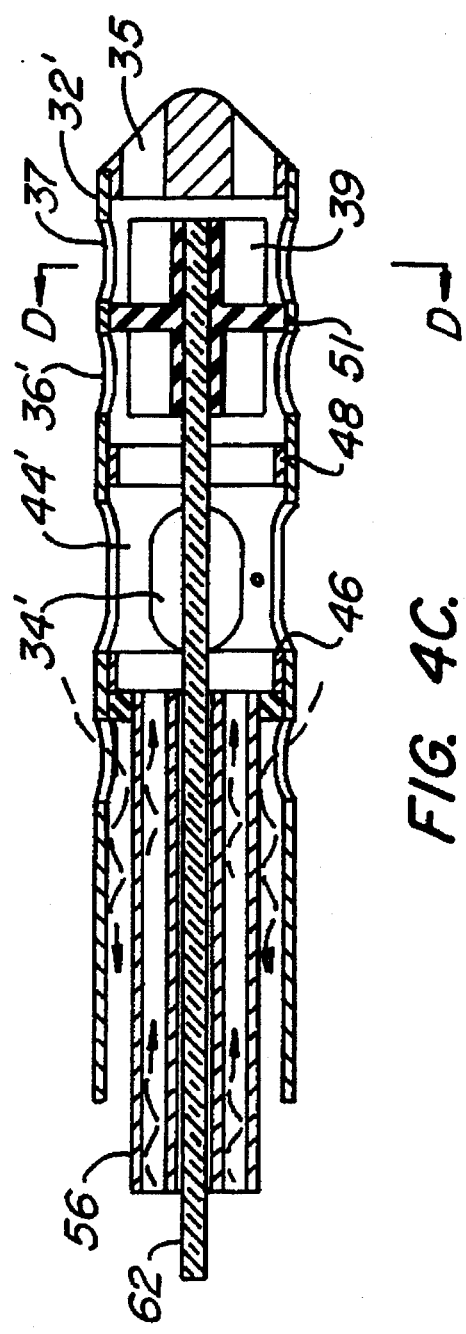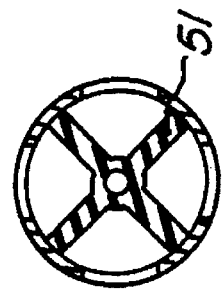

METHOD AND SYSTEM FOR DIRECT HEATING OF FLUID SOLUTION IN A HOLLOW BODY ORGAN

BACKGROUND OF THE INVENTION

1. Field of the Invention

The present invention relates generally to the field of thermal ablation where heat is delivered to necrose or ablate a diseased body organ. More specifically, the invention provides methods and devices for thermally ablating hollow body organs, such as the uterus, by heating a thermally conductive fluid disposed within the organ.

"Minimally invasive" surgical procedures have recently been developed as alternatives to conventional "open" surgery. Of particular interest to the present invention are minimally invasive surgical procedures relating to thermal treatment of hollow body organs, and particularly to treatment of the uterus. A variety of such thermal treatment procedures have been proposed which rely on a catheter to deliver heat to the interior of hollow body organs which are filled with a thermally conductive fluid. The heated fluid is then employed to heat the mucosa sufficient to induce injury and necrosis of the organ. For example, U.S. Pat. Nos. 5,045,056; 5,100,388; 5,188,602; 5,222,938, and U.S. patent application Ser. Nos. 08/073,639 and 08/266,037, the complete disclosures which are herein incorporated by reference, describe catheters having a conductive heating element disposed on the catheter which heats a thermally conductive fluid by conventional thermal conduction to a temperature sufficient to destroy the mucosa or endothelial lining of the organ, resulting in deactivation of the organ.

Although workable, the use of such catheters having conductive heating elements at their distal ends to deliver heat within the uterus can be problematic in certain respects. For instance, heat distribution through the thermally conductive fluid can be non-uniform, thereby requiring an increase in the total amount of heat delivered to the fluid in order to assure that the temperature of all portions of the mucosa are raised above the threshold level necessary to induce injury and necrosis. However, such an increase in heat delivery may raise the temperature of some portions of the mucosa above a desired maximum temperature. Such excessive heating is undesirable in that it can in some cases result in injury to adjacent organs. As an alternative, some attempts have been made to induce an oscillatory flow between a lumen in the catheter and the organ in order to reduce the temperature gradient within the fluid. Although oscillatory mixing of the thermally conductive fluid enhances heat delivery to remote locations within the organ, mixing by inducing an oscillatory flow between the catheter lumen and the organ may be undesirable in some cases because it often creates pressure waves within the organ. Such pressure waves may be particularly problematic within the uterus because hot conductive fluid may be forced through the fallopian tubes and into the abdominal cavity, thereby potentially causing damage to adjacent organs. Oscillatory mixing is also undesirable because of potential blockage of the catheter lumen by blood clots or tissue particles that may be suspended in the fluid.

Another drawback to such conductive heating catheters is the limited capacity of their conductive heating elements to rapidly deliver necessary heat to the thermally conductive fluid. In order to deliver sufficient heat to remote portions of the organ lining, it may be necessary to raise the surface temperature of the heating element above a desired maximum temperature. However, excessive heating can result in fouling of the heating element as a result of coagulation and denaturing of blood and other proteins that may be present in the fluid, thereby reducing the heat transfer capacity of the heating element and increasing operating time.

Another problem experienced when attempting to thermally ablate a hollow body organ is the existence of air bubbles that may become trapped within the organ when introducing the thermally conductive fluid. Air bubbles trapped within the organ will tend to decrease the amount of heat transfer from the fluid to the endometrium. Further, in the case of the uterus, trapped air will tend to expand when it is heated and may cause the intrauterine fluid pressure to increase above the desired maximum, resulting in potential leakage through the fallopian tubes.

Hence, for these and other reasons, it would be desirable to provide improved methods and devices which would overcome or greatly reduce these and other problems. In particular, it would be desirable to provide methods and devices having improved heat transfer characteristics so that adequate heat may rapidly be delivered to the fluid without fouling of the heating element. The methods and devices should also provide for a uniform heating of the fluid within the organ, preferably without undesirably increasing the intraorgan pressure. In one aspect, the devices will preferably be sufficiently small to allow introduction into the uterus through the cervical canal. Finally, the methods and devices should allow for the thermally conductive fluid to be introduced into the uterine cavity within a desired pressure range and so that air bubbles do not become trapped within the uterus.

2. Brief Description of the Background Art

As previously described, U.S. Pat. Nos. 5,045,056; 5,100, 388; 5,188,602; and 5,222,938 describe catheters having a conductive heating element that conductively heats a thermally conductive fluid within a hollow body organ.

U.S. Pat. No. 4,676,258 describes a device for radio frequency hyperthermia having a first electrode disposed in a tract or organ and a second electrode disposed on an outer circumference of a person to heat a tumor or malignancy region deep inside the person.

U.S. Pat. No. 5,368,591 describes a balloon catheter having heating electrodes disposed within the balloon.

U.S. Pat. No. 5,257,977 describes a catheter for introducing a heated fluid into the urethra.

U.S. Pat. No. 5,242,390 describes a device for introducing a heated liquid into the uterus.

U.S. Pat. No. 5,195,965 describes a catheter having a balloon for receiving a heated liquid.

U.S. Pat. No. 5,159,925 describes a catheter for laparoscopic cholecystostomy and prostate or gall bladder oblation. The catheter includes a distensible bladder at its distal end for receiving a heated fluid.

U.S. Pat. No. 4,469,103 describes a system for applying localized infrared electromagnetic energy to an effected area of a body.

U.S. Pat. No. 5,277,201 describes an endometrial ablation apparatus having an electroconductive balloon at its distal end for extending the organ and making electrical contact with the endometrial lining to be destroyed.

U.S. Pat. No. 4,430,076 describes a uterine manipulative and injector device for uterine insertion. The device includes an inflatable member at its insertable end which may be inflated to seal the lower portion of the uterus to retain fluid or gas injected into the uterine cavity.

U.S. Pat. No. 4,375,220 describes a microwave applicator for intracavity treatment of cancer.

U.S. Pat. No. 4,979,948 describes a catheter having a capacitative balloon electrode which may be expanded by an electrolyte solution to conform and make contact with the mucosal layer.

PCT Application No. WO 81/03616 describes a microwave antenna system for intracavity insertion for inducing hyperthermia by microwave irradiation.

Christoph D. Becker et al., *Long Term Occlusion of the Porcine Cystic Duct by Means of Endoluminal Radio Frequency Electrocoagulation, Radiology* 1988, 167:63–68 and Christoph D. Becker et al., *Gall Bladder Ablation Through Radio Logic Intervention Choela and Experimental Alternative to Cholecystectomy, Radiology* 1989, 171:235–240 describe gall bladder procedures using radio frequency energy.

German Patent No. DE 4123-418-A and Soviet Union Patent No. 1319848A describe thermal urology procedures.

Daniel B. Fram et al., *In Vivo Radio Frequency Thermal Balloon Angioplasty of Porcine Coronary Arteries; Histologic Effects and Safety, American Heart Journal,* 1993, 126:969–978 describes a radio frequency balloon catheter having two electrodes located on the catheter shaft within a balloon lumen.

Product brochure *Heads Up, Heated Balloon Catheters,* Copyright 1994, describes a balloon catheter having fluid that is heated by radio frequency current flowing between electrodes disposed within the balloon.

William S. Yamanashi et al., *Properties of Electromagnetic Field Focusing Probe, The Journal of Vascular Diseases,* Nov. 1988, p. 953–954 describes an electromagnetic field focusing apparatus having a radio frequency generator, a solenoid coil, and a hand-held catheter probe for producing eddy currents in biological tissues.

SUMMARY OF THE INVENTION

The invention provides methods and devices for heating a thermally (and usually electrically) conductive medium within a hollow body organ, such as the uterus, to necrose or ablate the mucosa or endothelial lining. In one exemplary embodiment, a thermal ablation device is provided having an elongate member with a proximal end and a distal end. A heating apparatus is provided near the distal end of the elongate member which is constructed to heat a thermally conductive fluid without substantial direct heating of the heating apparatus, i.e. although the heating apparatus may experience some heating during heating of the thermally conductive fluid, it is not intended that heating apparatus be employed to heat the fluid by conduction. Hence, the temperature of the heating apparatus will usually be at or only slightly above the fluid temperature while heating the fluid. The thermal ablation device is further provided with a fluid circulator near the heating apparatus to circulate the thermally conductive fluid past the heating apparatus.

In one exemplary aspect, the heating apparatus comprises a pair of spaced-apart electrodes, which are preferably ring electrodes. A radio frequency power supply is provided to supply current to the electrodes. When operated, radio frequency current passes between the electrodes and through the thermally conductive fluid (which will also be electrically conductive). As the current flows through the fluid, the fluid's natural resistance to the flow of current will generate thermal energy that will heat the fluid, with the rate of energy delivery being dictated by the square of the current multiplied by the resistance of the fluid. This energy is directly dissipated into the thermally and electrically conductive fluid. Since the electrodes themselves do not generate heat, they will generally be at or near the temperature of the fluid and thus will not become fouled by coagulation or denaturing of blood or other proteins that may be present in the fluid.

In an alternative aspect, the heating apparatus comprises a wire coil. An alternating current power supply is provided to supply alternating current to the wire coil. The varying current supplied to the coil creates a varying magnetic flux within the fluid which in turn causes eddy currents in the fluids that generates heat and increases the temperature of the fluid. Although the wire coil may experience some degree of heating as current is passed through the coil, such heating will be limited so that fouling of the wire coil will not occur. In a further alternative, microwave energy may by employed to heat the thermally conductive fluid.

In one particularly preferable aspect, the fluid circulator comprises an impeller. The impeller is provided to circulate the fluid between the electrodes or through the wire coil to provide a uniform temperature distribution within the hollow body organ. The impeller is advantageous in eliminating the need for inducing an oscillatory flow into the hollow body organ to circulate the fluid. In this way, intrauterine pressure may be maintained generally constant during circulation. Further, circulation only within the cavity eliminates potential clogging problems that may occur when introducing an oscillatory flow through a catheter lumen. Moreover, the impeller may also be fashioned to cut up clots or tissue particles within the fluid which may affect the temperature distribution of the fluid.

In another exemplary aspect, the elongate member includes a heating chamber near the distal end, with the heating apparatus and the fluid circulator being disposed within the heating chamber. Preferably, the heating chamber includes an inlet and an outlet which are disposed such that the thermally and electrically conductive fluid may be drawn through the inlet, circulated past the heating apparatus and expelled through the outlet upon the operation of the fluid circulator. Preferably, at least a portion of the elongate member is constructed of a dialectic material to isolate the electrodes from the patient.

In another aspect, an electrically insulated elongate shaft is provided and is attached at a distal end to the impeller. The shaft extends through the central lumen of the elongate member so that the impeller may be rotated by a motor located outside the patient. In a further exemplary aspect, a pair of spaced-apart occlusion members are provided about the periphery of the elongate member. The occlusion members are provided for receiving the cervical os and for forming a seal to prevent the heated fluid from escaping through the cervical canal and into the vagina. One of the occlusion members is preferably axially translatable relative to the other occlusion member. Further, one of the occlusion members is preferably radially expansible so that it may be expanded to lodge against the internal os of the cervix after being introduced into the uterus.

In still a further aspect, the thermal ablation device is provided with a temperature sensor within the chamber. Alternatively, another temperature may be disposed on an exterior surface of the elongate member. In the event that the fluid temperature within the uterus exceeds a desired amount, the power to the heating apparatus may be discontinued. In still another aspect, the elongate member is provided with an inflow lumen and an outflow lumen. An open fluid reservoir is in communication with the inflow lumen, with the fluid reservoir holding a supply of the thermally conductive fluid. In this way, the fluid may be introduced into the hollow body organ through the inflow lumen, with gases within the hollow body being flushed through the outflow lumen. Since the fluid reservoir is open, intrauterine pressure is maintained at a generally constant pressure as dictated by the head of the fluid reservoir.

The invention provides a particularly preferable embodiment of a thermal ablation device having an elongate member with a proximal end, a distal end, and a heating chamber near the distal end. A pair of spaced-apart electrodes are disposed within the heating chamber. An impeller is also disposed within the heating chamber and is spaced-apart from the electrodes. In this manner, a thermally conductive fluid may be circulated between the electrodes upon operation of the impeller. Preferably, the electrodes will comprise ring electrodes, and a radio frequency power supply will be provided to supply current to the electrodes. The heating chamber will preferably include an inlet and an outlet which are disposed such that the thermally conductive fluid may be drawn through the inlet, circulated between the electrodes, and expelled through the outlet upon operation of the impeller.

The invention provides an exemplary method for thermally ablating a hollow body organ. According to the method, a thermally conductive fluid and a heating apparatus are introduced into the hollow body organ. The heating apparatus is then operated to heat the fluid within the hollow body organ, with the temperature of the heating apparatus generally not exceeding the temperature of the fluid while the fluid is being heated. While heating the fluid, the fluid is circulated within the hollow body organ without substantially varying the pressure within the hollow body organ. In this manner, the fluid may be quickly heated without fouling the heating apparatus. Further, generally uniform heat distribution may be obtained within the organ without substantially varying the internal pressure, which in turn may cause fluid to escape from the hollow body organ and damage adjacent organs.

In one aspect, the heating step comprises passing radio frequency current through the fluid. Alternatively, an alternating magnetic flux may be generated within the fluid to heat the fluid. In another exemplary aspect, the circulating step comprises rotating an impeller within the hollow body organ.

The invention provides a particularly preferable method for thermally ablating a hollow body organ by introducing a thermally conductive fluid into the hollow body organ. Radio frequency current is then passed through the fluid while the fluid is within the hollow body organ to heat the fluid. The fluid within the hollow body organ is circulated without substantially varying the pressure within the hollow body organ. Preferably, the heating step will comprise introducing a pair of spaced-apart electrodes into the hollow body organ and passing radio frequency current between the pair of electrodes. At the same time, an impeller will preferably be rotated within the hollow body organ to continuously circulate the fluid between the electrodes so that the fluid within the hollow body organ may be uniformly heated. Preferably, the impeller will be rotated in the range from about 10 k to 30 k revolutions per minute to circulate the fluid. In another aspect, the temperature of the fluid within the hollow body organ will preferably be monitored.

In one particularly preferable aspect, the hollow body organ will comprise the uterus. A seal will preferably be provided at the cervical os prior to circulating the fluid so that fluid will not undesirably leak through the cervical canal and into the vagina. To necrose the endothelial lining of the uterus, the fluid will preferably be heated until a substantially uniform temperature in the range from about 60° C. to 100° C. is obtained within the uterus. The intrauterine pressure will be maintained at a substantially constant pressure when circulating the fluid so that the fluid will not pass through the fallopian tubes where it may harm adjacent tissue. Preferably, the pressure will be maintained in the range from about 30 mmHg to 50 mmHg.

The hollow body organ will preferably be substantially completely filled with the fluid prior to heating and circulating the fluid. The fluid will preferably be introduced such that any gases within the hollow body organ will be flushed from the organ as the fluid is introduced into and fills the organ.

The invention provides an alternative method for thermally ablating a hollow body organ. According to the method, a thermally conductive fluid is introduced into the hollow body organ. An alternating magnetic flux is generated within the fluid to heat the fluid within the hollow body organ. The fluid is circulated within the hollow body organ without substantially varying the pressure within the hollow body organ. Preferably, the alternating magnetic flux will be generated by passing alternating current through a wire coil disposed within the hollow body organ. Such a magnetic flux causes eddy currents in the fluid which will generate heat to heat the fluid. Preferably, the fluid will be circulated through the wire coil to assist in uniformly distributing the heated fluid within the organ.

BRIEF DESCRIPTION OF THE DRAWINGS

FIG. 1 is a side view of an exemplary thermal ablation device according to the present invention.

FIG. 2 is an enlarged view of a distal end of the ablation device of FIG. 1.

FIG. 3 is a more detailed view of a distal tip of the ablation device of FIG. 1.

FIG. 3A is a cross-sectional view of the distal tip of the ablation apparatus of FIG. 3 taken along lines A—A.

FIG. 4 is a cross-sectional view of the distal tip of the ablation device of FIG. 3.

FIG. 4A is an alternative embodiment of the distal tip of the ablation device of FIG. 1.

FIG. 4B is a front view of the distal tip of FIG. 4A.

FIG. 4C is a cross-sectional view of the distal tip of FIG. 4A.

FIG. 4D is a cross-sectional view of the distal tip of FIG. 4C taken along lines D—D.

DETAILED DESCRIPTION OF THE SPECIFIC EMBODIMENTS

Figure 5:
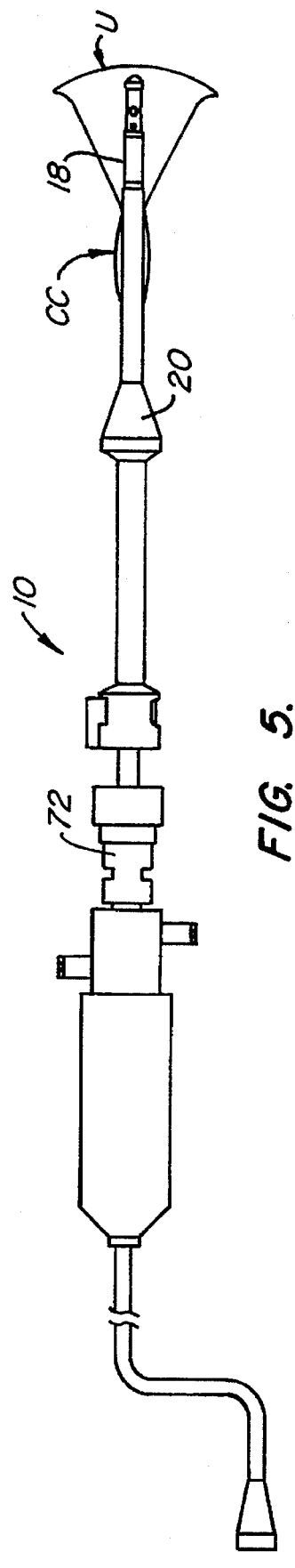
FIGS. 5 and 6 illustrate an exemplary method for introducing the ablation device of FIG. 1 into a uterus according to the present invention.

The invention provides methods and devices for heating a thermally conductive fluid within a hollow body organ to destroy the mucosa or endothelial lining of the organ. Usually, the thermally conductive fluid will also be electrically conductive, such as when employing radio frequency current to heat the fluid. Although useful in a wide variety of hollow body organs, the present invention will find its greatest use in treating the uterus.

Thermal ablation according to the invention begins by introducing a thermally conductive fluid, such as a saline solution, into the uterus. When the uterus is filled, the invention provides for heating the fluid with a heating apparatus that is constructed to heat the fluid without substantial direct heating of the heating apparatus. Preferably, the heater will be at about the same temperature or at a slightly higher temperature, i.e., within about 3° C., of the temperature of the fluid while the fluid is being heated. In this manner, fouling of the heater will not occur since the heater will not reach a temperature which is substantially above the temperature of the fluid. Usually, the maximum temperature of the heater and the fluid will be about 95° C. or less. Heating in such a manner is further advantageous in that increased power may be supplied to the heating apparatus so that the size of the heating apparatus may be reduced. Further, since the heating apparatus of the invention will not reach excessive temperatures, the heating apparatus may be disposed closer to tissue, thereby allowing the uterus to be filled with a smaller volume of the thermally conductive fluid. With less fluid in the uterus, the fluid will more rapidly reach its desired temperature, thereby further reducing the operating time. Moreover, reduction of the volume of fluid allows for improved heat distribution within the fluid.

In one preferable aspect, such a heating apparatus will comprise two or more electrodes that are located within the uterus and are directly exposed to the fluid held within the uterus. When electric current is flowed from one electrode, through the fluid, and to the second electrode, the fluid's natural resistance to the flow of electric current will generate thermal energy that will heat the fluid. The rate of energy delivery (P) is related to the current (I) and the resistance of the fluid (R) according to the equation: $P=I^2R$.

Alternatively, the present invention may produce such heating by providing an alternating magnetic flux within the fluid which will cause eddy currents in the fluid that generate heat. Such a magnetic flux will usually be created by introducing a wire coil into the uterus and passing high frequency alternating current through the coil. Preferably, the frequency of the current will be in the range from about 100 kHz to 300 kHz. Although the coil will experience some heating when the current is passed therethrough, the fluid will be heated substantially entirely by the resulting eddy currents rather than the temperature of the coil. When using a magnetic flux to heat the thermally conductive fluid, the fluid need not be electrically conductive.

To assist in uniformly distributing the heat created by the heating apparatus of the invention, the fluid will preferably be circulated past the heating apparatus and throughout the uterus. Such circulation will preferably be accomplished without substantially varying the intrauterine fluid pressure so that heated fluid will not be forced through the fallopian tubes and damage adjacent tissue or organs. Such circulation will best be accomplished by providing an impeller or similar device which draws fluid from the uterus and directs it across or through the heater where heating occurs. In this manner, the need for an oscillatory flow through a catheter is eliminated when circulating the fluid. Use of the impeller is further advantageous in that it may be employed to cut up clots or tissue particles which may be in the fluid and which can affect the temperature distribution within the uterus.

The uterus will preferably be filled substantially completely with the thermally and electrically conductive fluid so that virtually no air bubbles will remain within the uterus. Such filling is preferably best accomplished by flushing the air from the uterus when introducing the fluid. Preferably, an open fluid reservoir (i.e., the fluid reservoir will be open to the atmosphere) will be provided to introduce the fluid into the uterus. The open reservoir is advantageous in damping pressure variations that may occur within the uterus. Further, the open reservoir may be employed to control the amount of fluid pressure within the uterus by adjusting the head of the reservoir. Preferably, the intrauterine fluid pressure will remain constant and in the range from about 30 mmHg to 50 mmHg.

Referring now to FIG. 1, an exemplary embodiment of a thermal ablation device 10 will be described. The thermal ablation device 10 includes an elongate body 12 having a proximal end 14 and a distal end 16. The elongate body 12 may be constructed of a rigid material or a semiflexible material. Disposed near the distal end 16 is a radially expansible internal os seal 18. Axially spaced-apart from the internal os seal 18 is an external os seal 20. Between the internal os seal 18 and the external os seal 20 is a reduced diameter neck 22 for receiving the cervix. Construction of the internal os seal 18, the external os seal 20, and the neck 22 are described in copending application Ser. No. 08/266, 036, filed Jun. 27, 1994 (Attorney Docket No. 13178-27), the disclosure of which is herein incorporated by reference. Operation of the seals 18 and 20 will be described in greater detail hereinafter with reference to FIGS. 5 and 6.

Disposed in the elongate body 12 is a fluid inflow port 24 and a fluid outflow port 26 through which fluids may be introduced and withdrawn, respectively, to and from the uterus. The device 10 further includes a handle 28 which may optionally include an internal motor which is employed to circulate the fluid as described in greater detail hereinafter. At the proximal end 14 is a power supply connector 30 for connecting the device 10 to a radio frequency power supply as will be described in greater detail hereinafter.

Referring to FIG. 2, the distal end 16 of the device 10 will be described in greater detail. Distal to the internal os seal 18 is a distal tip 32 of the elongate body 12. The distal tip 32 may be constructed to be rigid or may alternatively be deflectable. Alternatively, the distal tip 32 may be angled relative to the elongate body 12. The distal tip 32 includes mixing inlets 34 and mixing outlets 36. As will be described in greater detail hereinafter, fluid within the uterus is drawn through mixing inlets 34, is heated within the device 10, and is then expelled back into the uterus through mixing outlets 36. A vent inlet 38 is provided and is in communication with the fluid outflow port 26 and serves to dampen pressure variations occurring within the uterus. The distal tip 32 is further provided with a blunt portion 40 to prevent tissue trauma when inserting the device 10 into the uterus.

Referring to FIGS. 3, 3A and 4, construction of the distal tip 32 will be described in greater detail. When fluid is introduced into the fluid inflow port 24, it passes through a pair of fluid inflow lumens 42 as illustrated by the dashed arrows. The incoming fluid exits the inflow lumens 42 and enters a heating chamber 44. Held within the heating chamber are a pair of spaced-apart ring electrodes 46, 48. Distal to the electrode 48 is an impeller 50. As fluid enters the heating chamber 44 from the inflow lumens 42, it passes through the electrode 46 and exists the chamber 44 through the mixing inlets 34 and mixing outlets 36. As fluid fills the uterus, gasses are removed from the uterus through exit ports 52 and into an annular fluid outflow lumen 54 where it may be withdrawn through the outflow port 26.

A multilumen tube 56 extends through the elongate body 12 and includes the fluid inflow lumens 42. A vent ring 58 is provided to isolate the fluid inflow lumens 42 from the fluid outflow lumen 54. The multilumen tube 56 further includes an electrode wire lumen 60 which serves as a conduit for electrode wires (not shown) connected to the electrodes 46, 48 and extending to the power supply connector 30.

To supply radio frequency current to the electrodes 46, 48, the power supply connector 30 is plugged into a conventional radio frequency power supply. Preferably, radio frequency current will be supplied at a frequency in that range from 200 kHz to 300 kHz. When radio frequency power is supplied to the electrodes 46, 48, current passes through the fluid within the heating chamber 44 to heat the fluid between the electrodes. The tubing of the elongate body 12 at the distal tip 32 is preferably constructed of a dialectic material so that the electrodes 46, 48 are electrically isolated from the patient. This protects the patient from unintended contact with the electrodes which may result in electric burns and fouling of the electrodes. The electrodes 46, 48 will preferably be constructed to maximize the surface area of the electrodes and the gap between the electrodes. The size of the electrodes 46, 48 and the distance therebetween will preferably be made as large as possible without exceeding size constraints for the distal tip 32. Usually, the distal tip 32 will have an outer diameter in the range from about 3 mm to 8 mm and a length in the range from about 10 mm to 30 mm. Maximizing the surface area and the gap increases the volume of fluid being heated by the electrodes 46, 48. In this way, more fluid may be heated more rapidly, and without fouling of the electrodes 46, 48.

As previously described, fluid is circulated through the heating chamber 44 by the impeller 50. The impeller 50 pulls fluid into the heating chamber 44 through the mixing inlets 34 where it passes between the electrodes 46, 48 for heating. The heated fluid then flows out of the device 10 through the mixing outlets 36 and circulates within the uterine cavity. The impeller will be fashioned so that it will efficiently pull fluid through the inlets 34 and expel the fluid from the outlets 36 without causing pressure waves within the uterus. Preferably, the impeller will be constructed of a 180° section of a coarse thread pitch screw. A drive shaft 62 is connected to the impeller 50 and extends through a drive shaft lumen 64 of the multilumen tube 56. The drive shaft 62 will preferably be constructed of a stainless steel rod. Alternatively, the drive shaft 62 may be constructed of a wound stainless steel a flexible plastic. A proximal end of the shaft 62 is connected to a DC electric motor, which preferably spins the impeller in the range from about 10,000 to 30,000 rpm, and more preferably, at about 25,000 rpm. As previously described, the DC electric motor may be included within the handle 28 or may be separate from the device 10. The drive shaft 62 is preferably electrically insulated, e.g. with teflon, to prevent current from traveling through the shaft which could reduce power input to the thermally conductive fluid and present a shock hazard. The impeller 50 is included within the elongate body 12 to prevent it from causing tissue trauma.

The impeller 50 will preferably be operated without substantially raising the intrauterine pressure. Preferably, the impeller 50 will be configured to circulate the fluid through the heating chamber 44 at a rate sufficient to ensure that a narrow temperature differential is maintained between the fluid within the heating chamber 44 and the fluid within the uterus. Circulation of the fluid in this manner also allows more energy to be input to the electrodes without overheating the fluid between them.

The size and number of the mixing inlets 34 and mixing outlets 36 will be configured to reduce the potential of tissue or blood clots becoming clogged therein. In the event that tissue or blood clots enter into the heating chamber 44, the impeller 50 will chop the tissue or clots into small morsels to further increase heat transfer capacity of the fluid.

The device 10 is further provided with at least one temperature sensor 66 located on the outside surface of the distal tip. The temperature sensor 66 may comprise a thermocouple, a thermistor, or the like. The temperature sensor 66 is located near the mixing inlets 34 so that the temperature of the fluid entering the inlets 34 may be detected. With information provided by the temperature sensor 66, power to the electrodes 46, 48 may be controlled to in turn control the intrauterine fluid temperature. Preferably, the fluid will be heated until reaching a temperature in the range from about 60° C. to 100° C.

As best shown in FIG. 4, an internal temperature sensor 68 is provided within the heating chamber 44 to monitor the temperature within the heating chamber 44. In the event that fluid is unable to circulate through the heating chamber 44, the fluid between the electrodes 46, 48 can super heat and exceed a desired maximum fluid temperature, usually at or exceeding about 100° C. If such an event occurs, the power to the electrodes 46, 48 may be shut off. Wiring for the sensors 66 and 68 extends through a lumen 70 in the multilumen tube 56 as best shown in FIG. 3A.

An alternative embodiment of a distal tip 32' is illustrated in FIGS. 4A-4D. The distal tip 32' is essentially identical to the distal tip 32 of FIGS. 3-4 except that the distal tip 32' houses a double impeller 51 and has an additional mixing inlets and outlets. The double impeller 51 is provided to increase fluid circulation within the uterine cavity and thus improve heat distribution. The distal tip 32' includes mixing inlets 34' which cooperate with mixing outlets 36' to circulate fluid through the mixing chamber 44' and past the electrodes 46, 48 in a manner similar to that previously described with the distal tip 32 of FIGS. 3-4. The distal tip 32' further includes mixing inlets 35 which cooperate with mixing outlets 37 to circulate fluid through a secondary chamber 39. The impeller 51 pulls fluid through the mixing inlets 35 and pushes the fluid out the mixing outlets 37. This essentially doubles fluid circulation within the uterine cavity and improves heat distribution. Preferably, the impeller will be constructed of two centrifugal impellers positioned back to back.

Figure 6:
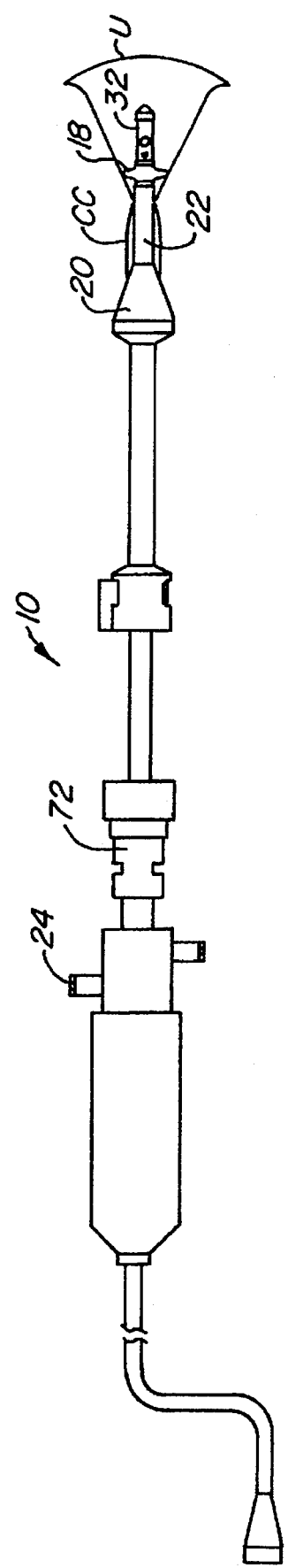

Referring to FIGS. 5 and 6, introduction of the thermal ablation device 10 into the uterus U through the cervical canal CC will be described. As shown in FIG. 5, the device 10 is transcervically introduced into the uterus U until the internal os seal 18 passes entirely through the cervical canal CC and into the uterus. An actuator 72 is then distally advanced to radially expand the internal os seal 18 as illustrated in FIG. 6. The device 10 is then proximally withdrawn to seat the internal os seal 18 against the internal os of the cervix. The external os seal 20 is then advanced to seat the seal 20 against the external os of the cervix, with the neck 22 lying within the cervical canal CC. The external os seal 20 is then locked to hold the seals 18, 20 in place. Once a suitable seal is formed, fluid is introduced into the uterus U through the inflow ports 24 as previously described. When the uterus U is filled with the fluid, heating may then proceed by energizing the electrodes as previously described. In this way, heating occurs within the uterus U so that heated fluid is not exposed to the cervical canal CC or to the vagina.

Figure 7:
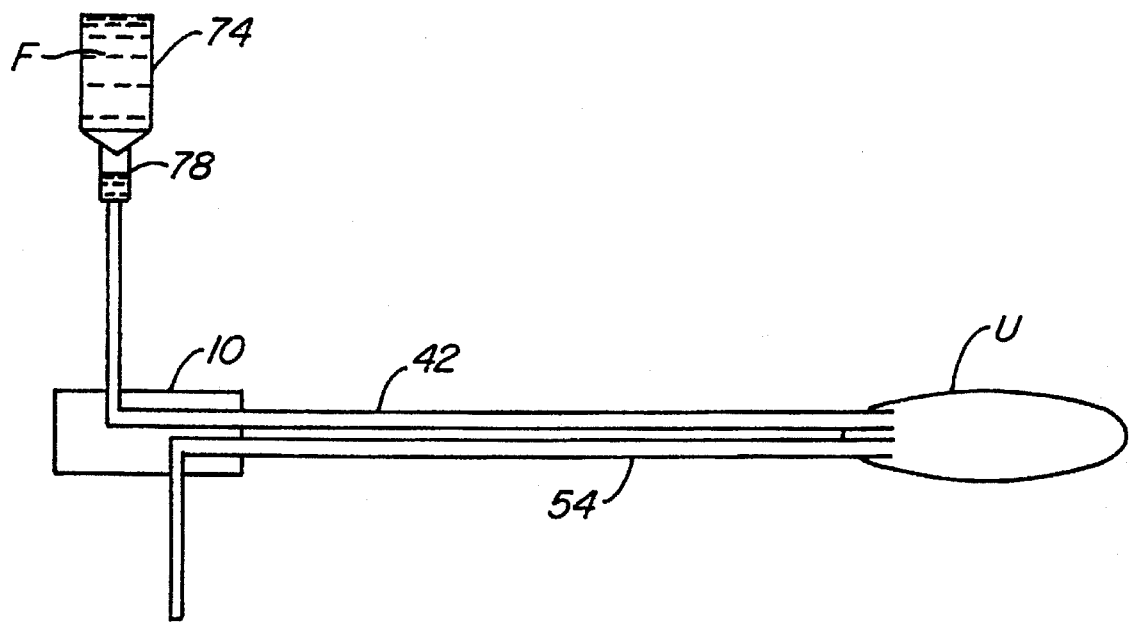
FIGS. 7–10 schematically illustrate an exemplary method for introducing a thermally conductive fluid into a hollow body organ according to the present invention.
Figure 8:
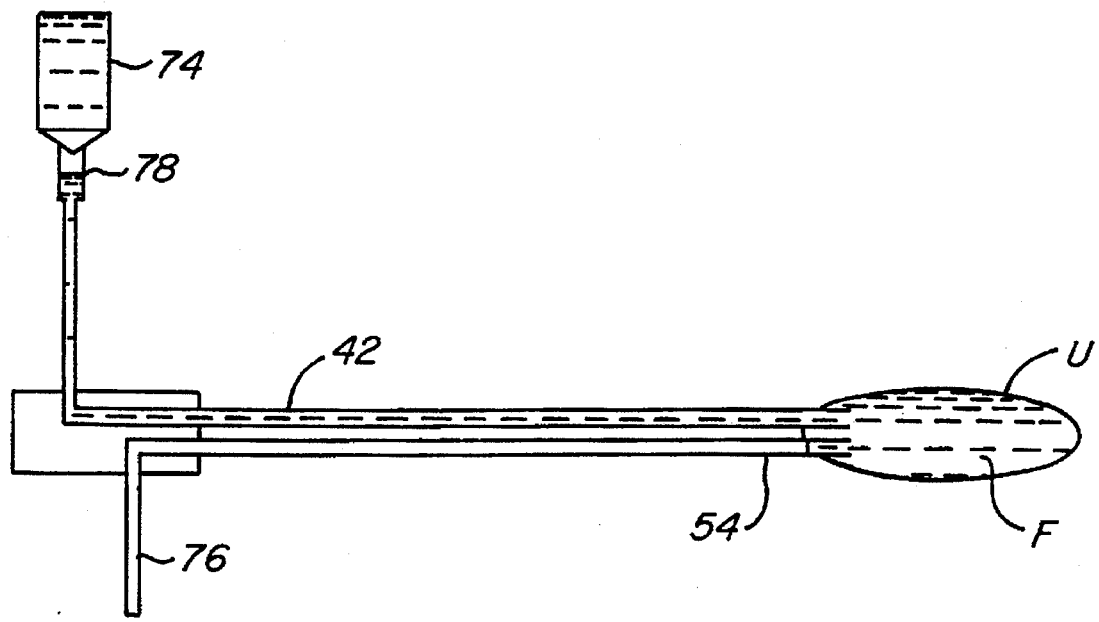
Figure 9:
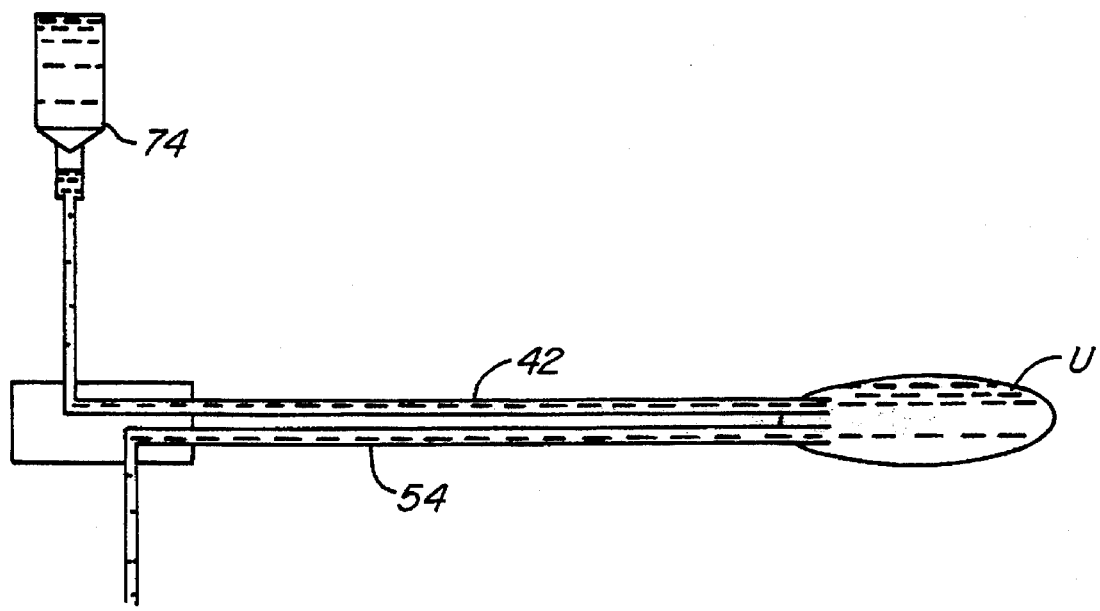
Figure 10:
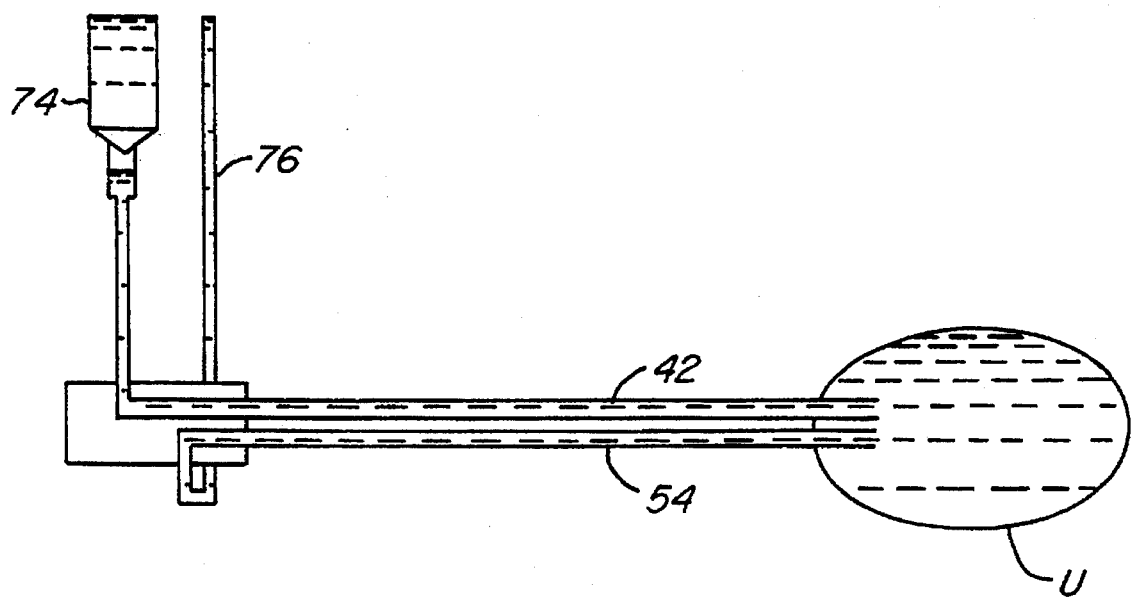

Referring to FIGS. 7-10, an exemplary method for filling the uterine cavity U with a thermally conductive fluid will be described. For convenience of discussion, reference numerals used to describe the thermal ablation device 10 will be used for like elements in the schematics of FIGS. 7–10. Operation of the thermal ablation device 10 to fill and maintain fluid within the uterus U will preferably proceed in a manner substantially identical to the procedure set forth schematically in FIG. 7–10. To fill the uterus U with fluid, an open fluid reservoir 74 having the fluid F is connected to the fluid inflow lumen 42 as shown in FIG. 7. Preferably, the fluid reservoir 74 will be elevated above the uterus U at a height sufficient to produce the desired intrauterine pressure. Preferably, the open fluid reservoir 74 will be an open saline bag that is elevated from about 16 inches to about 27 inches above the uterus to produce a pressure in the range from about 30 mmHg to 50 mmHg within the uterus U. As fluid flows through the inflow lumen 42, it enters the uterus U as illustrated in FIG. 8. Air within the uterus U is expelled through the outflow lumen 54. Optionally, the flow of fluid through the inflow lumen 42 may be restricted relative to the outflow lumen 54 to improve air removal from the uterus U. Further, a tube 76 may be attached to the outflow lumen 54 and hung below the uterus so that as fluid flows through the tube 76 a vacuum will be generated in the uterine cavity because of the restricted flow through the inflow lumen 42. The vacuum will tend to collapse the uterine cavity and suck the air from the uterus U. After the air is removed from the uterus U, the outflow lumen 54 will be primed and may be closed to allow the fluid F in the reservoir 74 to pressurize and distend the uterus U. If the intrauterine pressure unexpectedly increases, the excess pressure will naturally vent through the inflow lumen 42 and into the fluid reservoir 74. Further, as previously described, the vent inlet 38 on the device 10 is provided to allow undesirable pressure variations to be vented back through the fluid outflow port 26. In the unlikely event that fluid leaks from the uterine cavity, the fluid reservoir 74 may be employed to replenish the lost fluid to maintain the desired intrauterine pressure. Optionally, the reservoir 74 may be provided with a drip chamber 78 so that flow from the reservoir 74 can be monitored and controlled. As illustrated in FIG. 10, once the entire system is primed with the fluid F, the outflow tube 76 may be raised to the height of the fluid reservoir 74 to maintain the desired intrauterine pressure.

Figure 11:
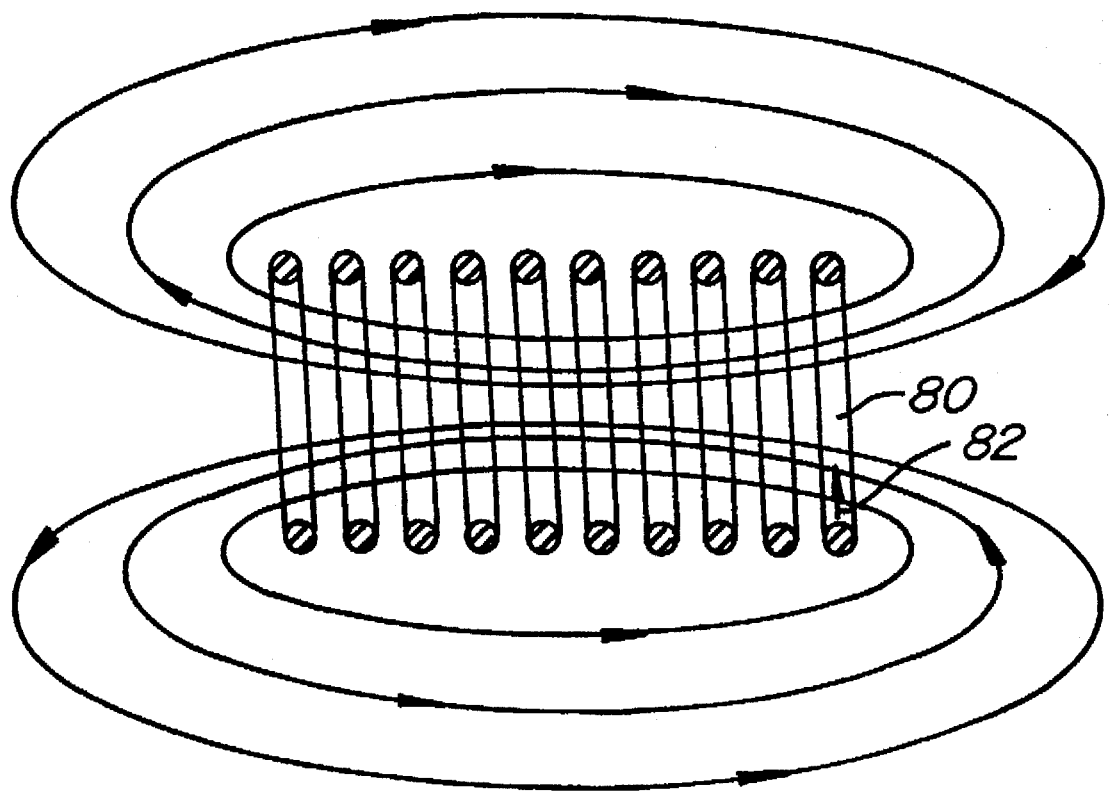
FIG. 11 is a cross-sectional view of a coil showing the distribution of magnetic flux when current is passed through the coil.

Referring to FIG. 11, a wire coil 80 is shown in cross-sectional view. The wire coil 80 may be employed as a substitute for the electrodes 46 and 48 of the thermal ablation device 10. To heat fluid using the wire coil 80, high frequency alternating current at a frequency in the range from 100 kHz to 300 kHz is directed through the wire coil in the direction indicated by the arrow 82. When electrical current is passed through the wire coil 80 in this manner, a magnetic flux is created. The magnetic flux distribution is illustrated with elliptical circles in FIG. 11, with the density of the flux being greatest inside the coil 80. The varying magnetic flux within the fluid in turn causes eddy currents in the fluid that generate heat. In this manner, fluid within the heating chamber 44 may be heated by the wire coil 80.

Although the foregoing invention has been described in detail for purposes of clarity of understanding, it will be obvious that certain modifications may be practiced within the scope of the appended claims.

What is claimed is:

1. A thermal ablation device for thermally ablating a hollow body organ, the device comprising:

an elongate member having a proximal end, a distal end, and a heating chamber near the distal end;

a heating apparatus operably attached to the elongate member near the distal end, the heating apparatus being constructed to heat a thermally conductive fluid without substantial direct heating of the heating apparatus; and a fluid circulator operably attached to the elongate member near the heating apparatus which circulates the thermally conductive fluid past the heating apparatus;

wherein the heating apparatus and the fluid circulator are disposed in the heating chamber, and wherein the heating chamber includes an inlet and an outlet which are exposed to the hollow body organ and which are disposed such that the thermally conductive fluid may be drawn through the inlet from the hollow body organ, circulated past the heating apparatus, expelled through the outlet into contact with the hollow body organ and recirculated through the inlet upon operation of the fluid circulator.

2. A thermal ablation device as in claim 1, wherein the fluid circulator comprises an impeller.

3. A thermal ablation device as in claim 2, wherein the impeller includes a proximal end and a distal end, wherein the elongate member includes a central lumen, and further comprising an insulated elongate shaft attached at the distal end of the impeller, said shaft extending through the central lumen of the elongate member.

4. A thermal ablation device as in claim 3, further comprising a motor for rotating the shaft.

5. A thermal ablation device as in claim 1, wherein the heating apparatus comprises a pair of spaced-apart electrodes.

6. A thermal ablation device as in claim 5, wherein the pair of electrodes comprise ring electrodes.

7. A thermal ablation device as in claim 6, further comprising a radio frequency power supply which supplies current to the electrodes.

8. A thermal ablation device as in claim 1, wherein the heating apparatus comprises a wire coil.

9. A thermal ablation device as in claim 8, further comprising an alternating current power supply which supplies alternating current to the wire coil.

10. A thermal ablation device as in claim 1, wherein at least a portion of the elongate member is constructed of a dielectric material.

11. A thermal ablation device as in claim 1, further comprising a pair of spaced apart occlusion members about the periphery of the elongate member for receiving the cervical os.

12. A thermal ablation device as in claim 11, wherein one of the occlusion members is axially translatable relative to the other occlusion member.

13. A thermal ablation device as in claim 11, wherein one of the occlusion members is radially expansible.

14. A thermal ablation device as in claim 1, further comprising a temperature sensor within the chamber.

15. A thermal ablation device as in claim 14, wherein the elongate member includes an exterior surface, and further comprising a temperature sensor disposed on the exterior surface of the elongate member.

16. A thermal ablation device as in claim 1, wherein the elongate member further includes an inflow lumen and an outflow lumen.

17. A thermal ablation device as in claim 16, further comprising an open fluid reservoir in communication with the inflow lumen, said fluid reservoir holding a supply of the thermally conductive fluid.

18. A thermal ablation device, comprising:

an elongate member having a proximal end and a distal end, wherein the elongate member defines a heating chamber near the distal end;

a pair of spaced-apart electrodes operably attached to the elongate member and disposed within the heating chamber;

an impeller operably attached to the elongate member, the impeller being disposed within the heating chamber and spaced-apart from the pair of electrodes, wherein a thermally and electrically conductive fluid may be circulated between the electrodes upon operation of the impeller; and a pair of spaced apart occlusion members about the periphery of the elongate member for receiving the cervical os, wherein one of the occlusion members is axially translatable relative to the other occlusion member.

19. A thermal ablation device as in claim 18, wherein the electrodes comprise ring electrodes.

20. A thermal ablation device as in claim 18, further comprising a radio frequency power supply which supplies current to the electrodes.

21. A thermal ablation device as in claim 18, wherein the heating chamber includes an inlet and an outlet which are disposed such that the thermally conductive fluid may be drawn through the inlet, circulated between the electrodes, and expelled through the outlet upon operation of the impeller.

22. A thermal ablation device as in claim 18, wherein at least a portion of the elongate member is constructed of a dielectric material.

23. A thermal ablation device as in claim 18, wherein the elongate member includes a central lumen, and further comprising an insulated elongate shaft attached at a distal end to the impeller, said shaft extending through the central lumen of the elongate member.

24. A thermal ablation device as in claim 23, further comprising a motor for rotating the shaft.

25. A thermal ablation device as in claim 18, wherein one of the occlusion members is radially expansible.

26. A thermal ablation device as in claim 18, further comprising a temperature sensor within the chamber.

27. A thermal ablation device as in claim 18, further comprising a temperature sensor disposed on an exterior surface of the elongate member.

28. A thermal ablation device as in claim 18, wherein the elongate member further includes an inflow lumen and an outflow lumen.

29. A thermal ablation device as in claim 28, further comprising an open fluid reservoir in communication with the inflow lumen, said fluid reservoir holding a supply of the thermally conductive fluid.

30. A method for thermally ablating a hollow body organ, said method comprising:

introducing a thermally conductive fluid and a heating apparatus having a fluid circulator into the hollow body organ so that the fluid circulator is within the hollow body organ;

operating the heating apparatus to heat the fluid within the hollow body organ, with the temperature of the heating apparatus generally not exceeding the temperature of the fluid while heating the fluid; and continuously circulating the fluid within the hollow body organ with the fluid circulator without substantially varying the pressure within the hollow body organ.

31. A method as in claim 30, wherein the thermally conductive fluid is also electrically conductive, and wherein the heating step comprises passing radio frequency current through the fluid.

32. A method as in claim 30, wherein the heating step comprises generating an alternating magnetic flux within the fluid.

33. A method as in claim 30, wherein the circulating step comprises rotating an impeller within the hollow body organ.

34. A method for thermally ablating a hollow body organ, said method comprising:

introducing a thermally and electrically conductive fluid into the hollow body organ;

passing radio frequency current through the fluid while the fluid is within the hollow body organ to heat the fluid; and circulating the fluid within the hollow body organ without substantially varying the pressure within the hollow body organ;

wherein the hollow body organ comprises the uterus, and further comprising heating the fluid until a substantially uniform temperature in the range from 60° C. to 100° C. is obtained within the uterus, and wherein the intrauterine pressure is in maintained at a substantially constant pressure in the range from 30 mmHg to 50 mmHg.

35. A method as in claim 34, wherein the heating step comprises introducing a pair of spaced-apart electrodes into the hollow body organ and passing radio frequency current between the pair of electrodes.

36. A method as in claim 34, wherein the circulating step comprises rotating impeller within the hollow body organ.

37. A method as in claim 36, wherein the impeller is rotated in the range from about 10,000 to 30,000 revolutions per minute.

38. A method as in claim 34, further comprising sensing the temperature within the hollow body organ.

39. A method as in claim 34, wherein the hollow body organ comprises the uterus, and further comprising sealing the uterus at the cervical os prior to circulating the fluid.

40. A method as in claim 34, further comprising filling the hollow body organ substantially completely with the fluid prior to heating and circulating the fluid.

41. A method as in claim 40, wherein the filling step comprises flushing any gasses from the hollow body organ while introducing the fluid into the hollow body organ.

42. A method for thermally ablating a hollow body organ, said method comprising:

introducing a thermally conductive fluid into the hollow body organ;

generating an alternating magnetic flux within the fluid to heat the fluid within the hollow body organ; and continuously circulating the fluid within the hollow body organ with a fluid circulator disposed within the hollow body organ without substantially varying the pressure within the hollow body organ.

43. A method as in claim 42, wherein the generating step comprises passing alternating current through a wire coil disposed within the hollow body organ.

44. A method as in claim 43, wherein the circulating step further comprises circulating the fluid through the wire coil.

45. A thermal ablation device, comprising:

an elongate member having a proximal end, a distal end, the elongate member defining a heating chamber near the distal end;

a pair of spaced-apart electrodes operably attached to the elongate member and disposed within the heating chamber;

an impeller operably attached to the elongate member, the impeller being disposed within the heating chamber and spaced-apart from the pair of electrodes, wherein a thermally and electrically conductive fluid may be circulated between the electrodes upon operation of the impeller; and a temperature sensor disposed on an exterior surface of the elongate member.

46. A method for thermally ablating a hollow body organ, said method comprising:

introducing a thermally conductive fluid and a heating apparatus having a fluid circulator into the hollow body organ so that the fluid circulator is within the hollow body organ;

operating the heating apparatus to heat the fluid within the hollow body organ, with the temperature of the heating apparatus generally not exceeding the temperature of the fluid while heating the fluid; and circulating the fluid within the hollow body organ without substantially varying the pressure within the hollow body organ, wherein the circulating step comprises rotating the impeller within the hollow body organ.

47. A method for thermally ablating a hollow body organ, said method comprising:

introducing a thermally and electrically conductive fluid into the hollow body organ;

passing radio frequency current through the fluid while the fluid is within the hollow body organ to heat the fluid; and circulating the fluid within the hollow body organ without substantially varying the pressure within the hollow body organ;

wherein the heating step comprises introducing a pair of spaced-apart electrodes into the hollow body organ and passing radio frequency current between the pair of electrodes.

48. A method for thermally ablating a hollow body organ, said method comprising:

introducing a thermally and electrically conductive fluid into the hollow body organ;

passing radio frequency current through the fluid while the fluid is within the hollow body organ to heat the fluid; and circulating the fluid within the hollow body organ without substantially varying the pressure within the hollow body organ, wherein the circulating step comprises rotating impeller within the hollow body organ.

49. A method as in claim 48, wherein the hollow body organ comprises the uterus, and further comprising heating the fluid until a substantially uniform temperature in the range from 60° C. to 100° C. is obtained within the uterus.

50. A method as in claim 49, wherein the intrauterine pressure is in maintained at a substantially constant pressure in the range from 30 mmHg to 50 mmHg.

* * * * *